United States Patent [19]

Floyd, Jr. et al.

[11] Patent Number: 4,536,517

[45] Date of Patent: Aug. 20, 1985

[54] METHOD OF TREATING DIABETES MELLITUS USING ARYLGLYOXALS

[75] Inventors: Middleton B. Floyd, Jr., Suffern; Jo A. Goidl, Spring Valley, both of N.Y.

[73] Assignee: American Cyanamid Company, Me.

[21] Appl. No.: 488,237

[22] Filed: Apr. 25, 1983

[51] Int. Cl.³ .......................................... A61K 31/185
[52] U.S. Cl. .................... 514/576; 514/866; 514/432; 514/438; 514/461; 514/471
[58] Field of Search ........................................ 424/315

[56] References Cited

PUBLICATIONS

J. of Med. & Pharm. Chem., vol. 1, No. 6, Feb. 1959, pp. 600–604.

Primary Examiner—Jerome D. Goldberg
Attorney, Agent, or Firm—Edward A. Conroy, Jr.

[57] ABSTRACT

A method of treating diabetes mellitus using arylglyoxals which are known compounds.

2 Claims, No Drawings

METHOD OF TREATING DIABETES MELLITUS USING ARYLGLYOXALS

BACKGROUND OF THE INVENTION

This invention relates to a method of treating diabetes mellitus using arylglyoxals and various hydrates and adducts formed from them. These compounds are either known in the art per se or are homologs or derivatives of compounds disclosed in the art. All the compounds of this invention are known in the art to have an unrelated pharmaceutical activity, or there is a disclosure of inactivity. The compounds of this invention are hypoglycemic agents capable of ameliorating diabetes mellitus in mammals by acting to simulate and/or potentiate the action of insulin. This invention further relates to pharmaceutical compositions for the utilization of these compounds in the treatment of diabetes mellitus. Further, this invention relates to the chemical synthesis of the compounds disclosed herein.

The disease diabetes mellitus is characterized by metabolic defects in the production and utilization of glucose which result in the failure to maintain appropriate blood sugar levels. The result of this defect is elevated blood glucose or hyperglycemia. Research on the treatment of diabetes has centered on attempts to normalize fasting and postprandial blood glucose levels. Treatments have included parenteral administration of exogenous insulin, oral administration of drugs, and dietary therapies.

Initially it was thought that hyperglycemia was simply the result of a deficiency in the supply of insulin, the principle hormone which controls glucose metabolism. As a result, research focused on the source of insulin production, the beta cells of the pancreas, and pharmaceutical agents were discovered which stimulated the production of insulin by the pancreas. Although it remains true that a deficiency of insulin does cause hyperglycemia it has now been recognized that other metabolic defects can be a major cause of elevated blood glucose.

In Type I diabetes, also called juvenile onset or insulin-dependent diabetes, insulin deficiency is indeed the cause of hyperglycemia. However, the majority of diabetics suffer from a form of the disease referred to as Type II diabetes, also called maturity onset or non-insulin dependent diabetes. A main characteristic displayed by Type II diabetics is insulin resistance or insulin insensitivity. Insulin resistance is a condition in which available insulin, secreted by the pancreas and circulating in the blood stream, fails to stimulate sufficient glucose uptake and utilization in insulin-sensitive tissue. This inability of certain tissues including liver, muscle, and fat, whose metabolic machinery is normally sensitive to insulin, to utilize glucose efficiently or to control endogenous glucose synthesis and glycogenolysis, results in elevated blood glucose.

Compounds which simulate and/or potentiate the biological action of insulin would be beneficial in the treatment of hyperglycemia resulting from mild to moderate insulin insufficiency or insulin insensitivity. A compound which would simulate or mimic insulin's action would correct both insulin deficiency and insulin resistance by its own insulin-like action. Further, a compound which would potentiate insulin's action would ameliorate insulin deficiency by rendering the small amount of insulin which is present more efficacious and would decrease insulin resistance directly by acting synergistically to make insulin more effective. Thus compounds which show insulin-like and/or insulin potentiating activity would be beneficial for the treatment of hypoglycemia occuring either in Type I or Type II diabetes.

The compounds of the present invention simulate and potentiate the biological action of insulin. They simulate insulin's action at least in part by promoting the cellular uptake and metabolism of glucose in the absence of insulin. They potentiate insulin's action by exerting a synergistic effect on insulin action in the presence of sub-maximal concentrations of insulin. The exact mechanism by which the compounds of the invention act to produce these effect is not known and the invention should not be construed as limited to any particular mechanism of action. Nonetheless, the compounds of this invention are useful for the treatment of hyperglycemia and diabetes in mammals.

BRIEF SUMMARY OF THE INVENTION

This invention is concerned with a method of treating diabetes mellitus with compounds which may be represented by the following structural formula:

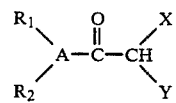

wherein A is selected from the group consisting of phenyl, 2-fluorenyl, 2-naphthyl, 2-dibenzofuranyl, 2-dibenzothienyl, 2-phenoxathiinyl, 2-phenanthryl, 3-phenanthryl, 9-phenanthryl, 2-thiophene, 2-thienyl and 9-anthracene; $R_1$ may be substituted meta or para to the aryl-carbonyl bond is selected from the group consisting of hydrogen, halogen, $(C_1-C_{20})$alkyl, $(C_1-C_{20})$alkoxy, cycloalkyl, phenyl, phenoxy, phenylthio, benzyl, $(C_1-C_{20})$alkyamino, substituted phenyl wherein the substituents are halogen, $(C_1-C_6)$alkyl or $(C_1-C_6)$alkoxy, substituted phenoxy wherein the substituents are halogen, $(C_1-C_6)$alkyl or $(C_1-C_6)$alkoxy, and substituted phenylthio wherein the substituents are halogen, $(C_1-C_6)$alkyl or $(C_1-C_6)$alkoxy; $R_2$ is selected from the group consisting of hydrogen and $(C_1-C_6)$alkoxy; X and Y may be the same or different and are independently selected from the group consisting of hydroxy, $(C_1-C_6)$alkoxy, anilino, carboxyanilino,

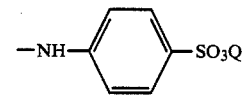

and $-SO_3Q$ wherein Q is an alkali metal or alkaline earth metal, with the proviso that X and Y taken together may represent oxygen; and the hydrates thereof.

This invention also relates to a method of treating hyperglycemia in a mammal in need of such treatment which comprises administering to said mammal an effective amount of a compound of the above-described formula.

This invention also relates to a pharmaceutical composition which comprises an effective antidiabetic amount of a compound of the above-described formula, in association with a pharmaceutically acceptable carrier.

This invention also relates to a pharmaceutical composition which comprises an effective hypoglycemic amount of a compound of the above-described formula in association with a pharmaceutically acceptable carrier.

Finally, this invention relates to processes for preparing compounds of the above-described formula.

In a more preferred embodiment, this invention is concerned with a method of treating diabetes mellitus with compounds represented by the above general formula wherein A is as described above; $R_1$ may be substituted meta or para to the aryl-carbonyl bond and is selected from the group consisting of hydrogen, chloro, fluoro, bromo, ($C_3$-$C_{16}$)alkyl, ($C_3$-$C_{16}$)alkoxy, cyclohexyl, phenyl, phenoxy, phenylthio, benzyl, ($C_4$-$C_{16}$)alkylamino, substituted phenyl wherein the substituents are selected from the group consisting of chloro, fluoro, bromo, methyl and methoxy; substituted phenoxy wherein the substituents are selected from the group consisting of chloro, fluoro, bromo, ($C_1$-$C_4$)alkyl and methoxy, substituted phenylthio wherein the substituents are selected from the group consisting of fluoro, chloro, ($C_1$-$C_4$)alkyl and methoxy; $R_2$ is selected from the group consisting of hydrogen and methoxy; X and Y may be the same or different and are independently selected from the group consisting of hydroxy, ethoxy, carboxyanilino,

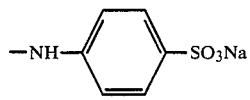

and —$SO_3Na$, with the proviso that X and Y taken together may represent oxygen; and the hydrates thereof.

DETAILED DESCRIPTION OF THE INVENTION

Certain of the compounds of this invention may be prepared according to the following reaction sequence:

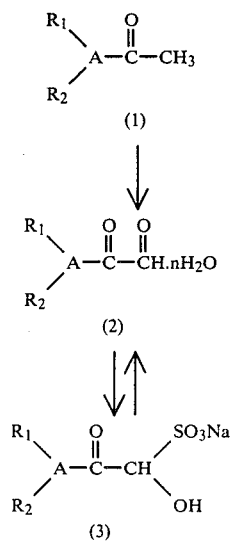

A ketone (1) is dissolved in dimethyl sulfoxide and treated with hydrobromic acid at 45°–65° C. for 18–48 hours. The mixture is poured into ice and extracted with ethyl acetate. The extract is concentrated, dissolved in a mixture of ethanol and water at 50°–70° C. and treated with sodium metabisulfite at the boiling point for 5 minutes, then cooled under argon at 0° C., giving (3) where $R_1$, $R_2$, and A are as described above. The methanesulfonic acid, sodium salt derivative (3) is then suspended in water at 40°–60° C., acidified, heated at 90°–100° C. for 1–2 hours, cooled and extracted with diethyl ether. The ether is concentrated giving (2) where $R_1$, $R_2$, and A are as described above. Compounds of structure (2) are obtained in various degrees of hydration; that is, n may vary from almost zero to one or more. Alternatively, the ketone (1), where $R_1$, $R_2$, and A are as described above, is treated with selenium dioxide in aqueous dioxane at reflux, under an inert atmosphere for 12–24 hours. The reaction is then filtered and the filtrate evaporated, giving (2) where $R_1$, $R_2$, and A are as described above which may be converted to the methanesulfonic acid, sodium salt derivative (3) by treatment with sodium metabisulfite in aqueous ethanol.

The compounds of this invention were tested for their insulin-like and insulin-potentiating activity according to the following procedure: Male, Wistar strain, Royal Hart rats weighing 125–170 g. were sacrificed by decapitation. Their abdominal cavities were opened and distal or thin portions of epididymal fat pads excised, accumulated, and placed in 0.9% saline. The tissue was weighed and placed at a density of about 0.4 g/ml in Krebs-Henseleit bicarbonate (KHB) buffer containing 5 mg. of crude bacterial collagenease per ml. [The KHB is composed of 118 mM sodium chloride; 4.7 mM potassium chloride; 1.2 mM calcium chloride; 1.2 mM potassium dihydrogen phosphate; 1.2 mM magnesium sulfate heptahydrate; 25 mM sodium bicarbonate and 0.3 mM glucose and is saturated with oxygen:carbon dioxide (95:5).] The tissues were incubated with collagenase for one hour at 37° C. with gentle agitation in a Dubnoff metabolic shaker. At the end of this digestion period the cells were washed five times with twice their volume of KHB buffer containing fatty acid free bovine serum albumin (Pentex Fraction V) at a concentration of 3%. The digest was filtered through two layers of gauze and suspended in KHB buffer with albumin to a volume ten times the initial total weight of the fat pads. Incubation of one ml. aliquots of the cell suspension was carried out in 17×100 mm plastic Falcon tubes. Cells were incubated in the presence or absence of test compound and insulin. All tubes contained 0.15 $\mu$Ci D-glucose-U-$^{14}$C (specific activity 200 mC/mmole).

Recrystallized porcine insulin (specific activity =25.5 U/mg) was dissolved in 0.9% saline adjusted to pH 3 with hydrochloric acid. The insulin was added to the cells at a concentration of approximately 5 $\mu$U/ml and control or basal cells received comparable volumes of pH 3 saline. Test compounds were dissolved in 50% dimethylsulfoxide-50% ethanol and added to the cells at a concentration of 100 $\mu$g/ml. Control cells received comparable volumes of dimethyl sulfoxide-ethanol.

After the tubes were loaded with insulin and test compound, or other vehicles, and cell suspension, they were capped with sleeve stoppers fitted with hanging, plastic center wells. Each well contained a small section of folded filter paper. The tubes were then gassed for about one minute with oxygen:carbon dioxide (95:5) via needles inserted through the septum of the stopper.

Immediately after gassing, the radioactive glucose was injected into the incubate and the tubes were placed in a 37° C. metabolic shaking water bath and were incubated for one hour with gentle agitation.

At the end of the incubation, 0.4 ml. of Hyamine hydroxide and then 0.5 ml. of 5N sulfuric acid were carefully injected into the center well and cell suspension, respectively. The acidified cell suspension was then incubated an additional 30 minutes at room temperature with gentle agitation. At the end of this carbon dioxide collection period, the center wells were dropped into vials containing 10 ml. of Dimiscint® scintillation cocktail and the radioactivity counted by liquid scintillation spectrometry.

The measurement of carbon dioxide radioactivity in counts per minute produced by these cells in the absence of both test compound and insulin is the basal level (b). Radioactivity produced in the presence of test compounds only, insulin only and both test compound and insulin are (c), (i) and (ci), respectively. Each of (c), (i) and (ci) is then expressed as a percent of the basal value: $C=(c/b)$; $I=(i/b)$; $CI=(ci/b)$. Finally, insulin-like activity (%C/I) is calculated using the formula $$\% C/I = \frac{(100)(C - 100)}{(I - 100)};$$

and insulin-potentiating activity (%P) is calculated using the formula $$\% P = \frac{(100)(CI - C - I + 100)}{(I - 100)}.$$

The results of this test on representative compounds of this invention appear in Table I.

TABLE I

| Compound | % C/I | % P |
|---|---|---|
| 4-biphenylglyoxal hemihydrate | 448 | 174 |
| p-[α-hydroxy-p-phenylphenacyl)amino]-benzoic acid | 166 | 222 |
| p-[(α-ethoxy-p-phenylphenacyl)amino]-benzoic acid | 119 | 244 |
| (4-biphenylcarbonyl)hydroxy-methanesulfonic acid, sodium salt | 165 | 125 |
| phenylglyoxal | 120 | 68 |
| p-chlorophenylglyoxal | 357 | 122 |
| benzoylhydroxy-methanesulfonic acid, sodium salt | 138 | 16 |
| 4'-(p-chlorophenyl)-2,2-dihydroxy-acetophenone | 572 | 0 |
| 4'-chloro-α-hydroxy-β-oxo-4-biphenylethane-sulfonic acid, sodium salt | 173 | 93 |
| 4'-heptyl-2,2-dihydroxy-acetophenone | 525 | 86 |
| p-cyclohexylbenzoylhydroxy-methanesulfonic acid, sodium salt | 612 | 33 |
| 4-cyclohexyl-2,2-dihydroxy-acetophenone | 788 | 0 |
| p-heptylbenzoylhydroxy-methanesulfonic acid, sodium salt | 315 | 241 |
| hydroxy(p-phenoxybenzoyl)-methanesulfonic acid, sodium salt | 188 | 259 |
| 2,2-dihydroxy-4'-phenoxy-acetophenone | 422 | 246 |
| hydroxy(4'-methoxy-4-biphenylcarbonyl)-methanesulfonic acid, sodium salt | 86 | 0 |
| (4'-fluoro-4-biphenylcarbonyl)hydroxy-methanesulfonic acid, sodium salt | 281 | 132 |
| 2,2-dihydroxy-4'-p-tolyl-acetophenone | 240 | 141 |
| 2-fluorenyl-dihydroxymethyl ketone | 304 | 131 |
| p-[[hydroxy(2-naphthoyl)methyl]amino]-benzoic acid | 371 | 190 |
| hydroxy(4'-methyl-4-biphenylcarbonyl)-methanesulfonic acid, sodium salt | 57 | 49 |
| α-hydroxy-β-oxo-fluorene-2-ethanesulfonic acid, sodium salt | 73 | 131 |
| α-hydroxy-β-oxo-2-dibenzofuranethanesulfonic acid, sodium salt | 130 | 133 |
| α-hydroxy-β-oxo-2-phenoxathiinethanesulfonic acid, sodium salt | 50 | 15 |
| dihydroxymethyl-2-phenoxathiinyl ketone | 185 | 56 |
| p-bromobenzoylhydroxy-methanesulfonic acid, sodium salt | 31 | 124 |
| α-hydroxy-β-oxo-3-biphenylethanesulfonic acid, sodium salt | 494 | 293 |
| 4'-(o-bromophenyl)-2,2-dihydroxy-acetophenone | 356 | 152 |
| 2'-chloro-α-hydroxy-β-oxo-4-biphenylethane-sulfonic acid, sodium salt | 163 | 123 |
| 2-dibenzofuranyloxyaldehyde | 75 | 75 |
| 2-dibenzothienyl-ethoxyhydroxymethyl ketone | 389 | 0 |
| α-hydroxy-β-oxo-2-benzothiopheneethanesulfonic acid, sodium salt | 193 | 120 |
| α-hydroxy-β-oxo-9-phenanthreneethanesulfonic acid, sodium salt | 39 | 37 |
| dihydroxymethyl-9-phenanthryl ketone | 99 | 0 |
| N—(α-hydroxy-p-phenylphenacyl)-sulfanilic acid, sodium salt | 39 | 81 |
| α-hydroxy-6-methoxy-β-oxo-3-biphenylethane-sulfonic acid, sodium salt | 124 | 49 |
| dihydroxymethyl-3-phenanthryl ketone | 357 | 93 |
| α-hydroxy-β-oxo-9-anthraceneethanesulfonic acid, sodium salt | 39 | 0 |
| α-hydroxy-β-oxo-2-phenanthreneethanesulfonic acid, sodium salt | 111 | 38 |
| 2-thiopheneglyoxylaldehyde | 40 | 0 |
| dihydroxymethyl-5-phenyl-2-thienyl ketone | 220 | 0 |
| α-hydroxy-β-oxo-3-phenanthreneethanesulfonic acid, sodium salt | 140 | 68 |
| α-hydroxy-β-oxo-5-phenyl-2-thiopheneethane-sulfonic acid sodium salt | 163 | 25 |
| hydroxy[p-(phenylthio)benzoyl]-methanesulfonic acid, sodium salt | 90 | 201 |
| (p-chlorobenzoyl)hydroxy-methanesulfonic acid, sodium salt | 164 | 122 |
| (p-benzylphenyl)glyoxylaldehyde | 245 | 127 |
| p-benzylbenzoxylhydroxy-methanesulfonic acid, sodium salt | 62 | 137 |
| dihydroxymethyl-2-phenanthryl ketone | 153 | 34 |
| 4'-(p-chlorophenoxy)-2,2-dihydroxy-acetophenone | 285 | 44 |
| [p-(p-chlorophenoxy)benzoyl]hydroxy-methanesulfonic acid, sodium salt | 87 | 136 |
| [p-(p-tert.-butylphenoxy)benzoyl]hydroxy-methanesulfonic acid, sodium salt | 119 | 55 |
| (p-fluorophenyl)-glyoxal | 85 | 10 |
| p-fluorobenzoylhydroxy-methanesulfonic acid, sodium salt | 116 | 71 |
| p-anisoylhydroxy-methanesulfonic acid, sodium salt | 67 | 0 |
| [p-(decyloxy)phenyl]-glyoxal | 398 | 159 |
| 4'-(hexadecyloxy)-2,2-dihydroxy-acetophenone | 64 | 106 |
| 4'-(p-tert.-butylphenoxy)-2,2-dihydroxy-acetophenone | 671 | 214 |
| [p-(p-fluorophenoxy)phenyl]-glyoxal | 698 | 192 |
| 2,2-dihydroxy-4'-(p-methoxyphenoxy)-acetophenone | 414 | 78 |
| hydroxy[p-(p-methoxyphenoxy)benzoyl]-methane sulfonic acid, sodium salt | 163 | 79 |
| 2,2-dihydroxy-4'-methoxy-acetophenone | 172 | 178 |
| [p-(decyloxy)benzoyl]hydroxy-methanesulfonic acid, sodium salt | 433 | 282 |
| (p-butoxyphenyl)glyoxal | 672 | 266 |
| p-butoxybenzoylhydroxy-methanesulfonic acid, sodium salt | 296 | 350 |
| [p-(p-fluorophenoxy)benzoyl]hydroxy-methane sulfonic acid, sodium salt | 458 | 309 |
| p-[[2-(2-dibenzofuranyl)-1-hydroxy-2-oxoethyl]amino]benzoic acid | 334 | 136 |
| 4'-(p-bromophenoxy)-2,2-dihydroxy-acetophenone | 297 | 216 |
| [p-(p-tert.-butylphenylthio)benzoyl]hydroxy-methanesulfonic acid, sodium salt | 79 | 46 |
| hydroxy[p-(p-methoxyphenylthio)benzoyl]-methanesulfonic acid, sodium salt | 139 | 158 |
| [p-(hexadecyloxy)benzoyl]hydroxy-methane sulfonic acid, sodium salt | 198 | 275 |
| [p-(decylamino)benzoyl]hydroxy-methanesulfonic acid, sodium salt | 166 | 146 |

TABLE I-continued

| Compound | % C/I | % P |
|---|---|---|
| hydroxy[p-(m-tolyloxy)benzoyl]-methanesulfonic acid, sodium salt | 400 | 548 |
| hydroxy(p-tolyloxybenzoyl)-methanesulfonic acid, sodium salt | 113 | 162 |
| [p-(p-fluorophenylthio)benzoyl]hydroxy-methanesulfonic acid, sodium salt | 367 | 493 |
| [p-(m-chlorophenoxy)benzoyl]hydroxy-methanesulfonic acid, sodium salt | 528 | 550 |
| hydroxy[p-(p-tolylthio)benzoyl]-methane sulfonic acid, sodium salt | 227 | 348 |
| 2,2-dihydroxy-4'-p-tolyloxy-acetophenone | 580 | 188 |
| 2,2-dihydroxy-4'-m-tolyloxy-acetophenone | 1032 | 188 |
| hydroxy[p-(m-methoxyphenoxy)benzoyl]-methanesulfonic acid, sodium salt | 53 | 127 |
| hydroxy(p-propoxybenzoyl)-methanesulfonic acid, sodium salt | 254 | 185 |
| (p-aminobutylbenzoyl)hydroxy-methanesulfonic acid, sodium salt | 133 | 132 |
| [p-(p-chlorophenylthio)benzoyl]hydroxy-methanesulfonic acid, sodium salt | 156 | 263 |
| [p-(m-fluorophenoxy)benzoyl]hydroxy-methanesulfonic acid, sodium salt | 208 | 399 |
| hydroxy(p-pentyloxybenzoyl)-methanesulfonic acid, sodium salt | 582 | 644 |
| 2,2-dihydroxy-4'-propoxy-acetophenone | 227 | 89 |
| 4'-(m-chlorophenoxy)-2,2-dihydroxy-acetophenone | 751 | 283 |
| o-bromobenzoylhydroxy-methanesulfonic acid, sodium salt | 88 | 59 |
| 2,2-dihydroxy-4'-(octyloxy)-acetophenone | 761 | 283 |
| 2,2-dihydroxy-4'-(isopentyloxy)-acetophenone | 463 | 169 |
| 4'-hexadecylamino-2,2-dihydroxy-acetophenone | 273 | 175 |
| α-hydroxy-3-(4-methylphenoxy)-β-oxo-benzeneethanesulfonic acid, sodium salt | 83 | 113 |
| 4-(decylamino)-α-oxo-benzeneacetaldehyde | 349 | 29 |
| 4-(hexadecylamino)-α-hydroxy-β-oxo-benzeneethanesulfonic acid, sodium salt | 446 | 391 |
| [p-(p-bromophenoxy)benzoyl]hydroxy-methanesulfonic acid, sodium salt | 57 | 158 |
| hydroxy[p-(octyloxy)benzoyl]-methanesulfonic acid, sodium salt | 223 | 77 |
| 3-[4-(1,1-dimethylethyl)phenoxy]-α-hydroxy-β-oxo-benzeneethanesulfonic acid, sodium salt | 135 | 107 |
| hydroxy[p-(isopentyloxy)benzoyl]-methane-sulfonic acid, sodium salt | 250 | 315 |

When the compounds are employed for the above utility, they may be combined with one or more pharmaceutically acceptable carriers, e.g., solvents, diluents and the like, and may be administered orally in such forms as tablets, capsules, dispersible powders, granules, or suspensions containing, for example, from about 0.5 to 5% of suspending agent, syrups containing, for example, from about 10 to 50% of sugar, and elixirs containing, for example, from about 20 to 50% ethanol, and the like, or parenterally in the form of sterile injectable solutions or suspensions containing from about 0.5 to 5% suspending agent in an isotonic medium. These pharmaceutical preparations may contain, for example, from about 0.5% up to about 90% of the active ingredient in combination with the carrier, more usually between 5% and 60% by weight.

The effective dosage of active ingredient employed may vary depending on the particular compound employed, the mode of administration and the severity of the condition being treated. However, in general, satisfactory results are obtained when the compounds of the invention are administered at a daily dosage of from about 5 milligrams to about 100 milligrams per kilogram of animal body weight, preferably given in divided doses two to four times a day, or in sustained release form. For most large mammals, the total daily dosage is from about 500 milligrams to about 5,000 milligrams preferably from about 350 milligrams to 3,500 milligrams. Dosage forms suitable for internal use comprise from about 25 to 500 milligrams of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapetuic situation. A decided practical advantage is that these active compounds may be administered orally as well as by intravenous, intramuscular, or subcutaneous routes if necessary. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and anti-oxidants, e.g., vitamin E, ascorbic acid, BHT and BHA.

The preferred pharmaceutical compositions from the stand-point of ease of preparation and administration are solid composition, particularly tablets and hard-filled or liquid-fiiled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropylcellulose. Dispersions can also be prepared in glycerol, liquid polyethylene glycols, and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be solvent or dispersion medium containing, for example, water, ethanol, polyol (e.g., glycerol, propylene glycol and liquid polyethylene glycol), suitable mixtures thereof, and vegetable oils.

The invention will be more fully described in conjunction with the following specific examples which are not to be construed as limiting the scope of the invention.

EXAMPLE 1

4'-Propoxyacetophenone

A mixture of 12.3 g. of 1-propyl bromide, 13.6 g. of 4-hydroxyacetophenone, 27.6 g. of potassium carbonate and 200 ml. of acetone was refluxed overnight. The mixture was then cooled, filtered, the filtrate concentrated and distilled in a Kugelrohr. The distillate was dissolved in ethyl acetate, treated with charcoal, filtered through diatomaceous earth, concentrated and dried, giving the desired intermediate as an oil.

Following essentially the procedure of Example 1, but employing other starting materials, the intermediates of Examples 2-18 (Table II) were obtained.

TABLE II

| Example | Intermediate | Physical Constant |
| --- | --- | --- |
| 2 | 4'-(decyloxy)acetophenone | mp 35-36° C. |
| 3 | 4'(phenylthio)acetophenone | mp 66.5-68.5° C. |
| 4 | 4'-(p-methoxyphenoxy)acetophenone | mp 48-51 |
| 5 | 4'(p-bromophenoxy)acetophenone | mp 67-73° C. |
| 6 | 4'-(p-tert-butylpheylthio)-acetophenone | mp 48-51° |
| 7 | 4'-(p-methoxylphenythio)-acetophenone | mp 31-34° C. |
| 8 | 4'-(p-fluorophenylthio)-acetophenone | mp 62-68° C. |
| 9 | 4'-(m-chlorophenoxy)acetophenone | bp 156-158° C. |
| 10 | 4'-butylaminoacetophenone | mp 78-81° C. |
| 11 | 4'-(p-chlorophenylthio)-acetophenone | mp 45-50° C. |
| 12 | 4'-n-hexadecyloxyacetophenone | mp 62-64° C. |
| 13 | 4'-m-tolyloxy)acetophenone | bp 143-145° C. |
| 14 | 4'-(p-tolylthio)acetophenone | mp 81-85° C. |
| 15 | 4'-(p-tolyloxy)acetophenone | mp 41-44° C. |
| 16 | 4'-(p-octyloxy)acetophenone | mp 27-29° |
| 17 | 4'-(isopentyloxy)acetophenone | oil |
| 18 | 4'-(m-fluorophenoxy)acetophenone | bp 131° C. |

EXAMPLE 19

2-Bromo-4'(-p-tolyl)acetophenone

An 11.7 g. portion of 4-methylbiphenyl was dissolved in 75 ml. of carbon disulfide and cooled in an ice bath while 11.6 g. of aluminum chloride was added portionwise with vigorous stirring. A 15.9 g. portion of bromoacetylbromide was added dropwise and after completion and the reaction subsided the mixture was heated at reflux for 3 hours, then cooled overnight. The mixture was poured into crushed ice and 150 ml. of acetic acid and stirred for 1.5 hours. The resulting gum was collected and stirred in methanol for 2 hours, giving a solid. This solid was dissolved in methanol:acetone, treated with charcoal and cooled. The solution was decanted, concentrated to about 150 ml., decanted and recooled giving a solid which was collected, giving the desired intermediate as a beige solid, m.p. 120°-122° C.

Following essentially the procedure of Example 19, but employing other starting materials, the intermediates of Examples 20-30 (Table III) were obtained.

TABLE III

| Example | Intermediate | Physical Constant |
| --- | --- | --- |
| 20 | 2-bromo-4'-(p-fluorophenyl)-acetophenone | mp 98.5-99.5° C. |
| 21 | 4'-(p-methoxyphenyl)acetophenone | mp 148-154° C. |
| 22 | 2-bromo-4'-(p-chlorophenyl)-acetophenone | mp 124-126° C. |
| 23 | 2-bromo-4'-cyclohexylacetophenone | mp 37.5-38° C. |
| 24 | 2-bromo-4'-heptylacetophenone | mp 35-36° C. |
| 25 | 4'-benzylacetophenone | bp 130-133° C. |
| 26 | 2-bromo-4'-(O—bromophenyl)-acetophenone | oil |
| 27 | 2-dibenzothienyl methyl ketone | mp 99-103° C. |
| 28 | 2-xanthenyl methyl ketone | mp 106-109° C. |

TABLE III-continued

| Example | Intermediate | Physical Constant |
| --- | --- | --- |
| 29 | 2-bromo-4'-methoxy-3'-phenyl-acetophenone | mp 76-77° C. |
| 30 | 2-dibenzofuranyl methyl ketone | mp 71-72° C. |

EXAMPLE 31

[p-(Decyloxy)phenyl]glyoxal

A mixture of 11.56 g. of 4'-(decyloxy)acetophenone, 4.6 g. of selenium dioxide, 150 ml. of dioxane and 4 ml. of water was refluxed overnight, filtered through diatomaceous earth, washed with dioxane and the filtrate evaporated to dryness. The residue was triturated with water, dried and crystallized from 150 ml. of hot acetone giving the desired product as an off-white solid, m.p. 81°-83° C.

EXAMPLE 32

[p-(decyloxy)benzoyl]hydroxymethanesulfonic acid, sodium salt

To a warm solution of 4.0 g. of [p-(decyloxy)phenyl]-glyoxal in 150 ml. of ethanol was added a solution of 1.045 g. of sodium metabisulfite in 20 ml. of water. The mixture was allowed to stand overnight and then the solid was collected, washed with acetone and dried. This solid was crystallized twice from a mixture of acetone:water (1.1), giving the desired product as a white solid.

EXAMPLE 33

Hydroxy[p-(isopentyloxy)benzoyl]methanesulfonic acid, sodium salt

A mixture of 9.4 g. of 4'-(isopentyloxy)acetophenone, 7.7 ml. of 48% hydrobromic acid and 38 ml. of dimethyl sulfoxide was stirred at 60° C. for 67 hours. The mixture was then cooled, poured into 200 ml. of ice water, 100 ml. of water was added and the solid was collected and washed with water. This solid was dissolved in acetone, filtered and precipitated by the addition of water. This solid was dissolved in 150 ml. of ethanol and a solution of 4.0 g. of sodium metabisulfite in 125 ml. of water, warmed and stirred for 2 hours, then stirred at room temperature overnight. The solid was collected giving the desired product.

EXAMPLE 34

2,2-dihydroxy-4'-(isopentyloxy)acetophenone

A 6.0 g. portion of hydroxy [p-(isopentyloxy)benzoyl]methanesulfonic acid, sodium salt was dissolved in a mixture of 100 ml. of 0.5N hydrochloric acid and 15 ml. of acetone. The solid was collected, giving the desired product, m.p. 80°-85° C.

Reaction of the intermediates of Examples 1-30, as well as other commercially available acetophenone derivatives and acetophenone derivatives made by the general procedures of Examples 1 and 19 according to the procedures of Examples 31-34, gave the products of Examples 35-115 (Table IV).

TABLE IV

| Example | Intermediate Derivation | Product | Physical Constant |
| --- | --- | --- | --- |
| 35 | 4-acetylbiphenyl | 4-biphenylglyoxal hemihydrate | mp 104-109° C. |

TABLE IV-continued

| Example | Intermediate Derivation | Product | Physical Constant |
|---|---|---|---|
| 36 | Phenyl-glyoxal | benzoylhydroxy-methanesulfonic acid, sodium salt | mp 174–180° C. |
| 37 | p-phenoxy-acetophenone | 2,2-dihydroxy-4'-phenoxyacetophenone | mp 73–80° C. |
| 38 | 37 | hydroxy (p-phenoxybenzoyl)-methanesulfonic acid, sodium salt | mp 170–180° C. |
| 39 | 21 | hydroxy (4'-methoxy-4-biphenylcarbonyl)-methanesulfonic acid, sodium salt | mp 205–220° C. |
| 40 | 20 | (4'-fluoro-4-biphenylcarbonyl)hydroxy-methanesulfonic acid, sodium salt | mp 195–205° C. |
| 41 | 2-acetyl-fluorene | 2-fluorenyl dihydroxymethyl ketone | mp 110–125° C. |
| 42 | 41 | α-hydroxy-β-oxo-fluorene-2-ethane-sulfonic acid, sodium salt | mp 250° C. |
| 43 | 30 | α-hydroxy-β-oxo-2-dibenzofuranethane-sulfonic acid, sodium salt | mp <300° C. |
| 44 | 28 | α-hydroxy-β-oxo-2-phenoxathiinethane-sulfonic acid, sodium salt | mp <300° |
| 45 | 44 | dihydroxymethyl 2-phenoxathiinyl ketone | mp 125–128° C. |
| 46 | 3-acetylbiphenyl | α-hydroxy-β-oxo-3-biphenylethane-sulfonic acid, sodium salt | mp 190–198° C. |
| 47 | 30 | 2-dibenzofuranglyoxylaldehyde | mp 120–123° C. |
| 48 | 27 | 2-dibenzothienyl ethoxyhydroxymethyl ketone | mp 82–85° C. |
| 49 | 48 | α-hydroxy-β-oxo-2-benzothiophene-ethanesulfonic acid, sodium salt | mp 210–220° C. |
| 50 | 9-acetyl-phenanthrene | α-hydroxy-β-oxo-9-phenanthreneethane-sulfonic acid, sodium salt | mp 185° C. (dec.) |
| 51 | 50 | dihydroxymethyl 9-phenanthryl ketone | mp 94–100° C. |
| 52 | 29 | α-hydroxy-6-methoxy-β-oxo-3-biphenyl-ethanesulfonic acid, sodium salt | mp 173° C. |
| 53 | 3-acetyl-phenanthrene | α-hydroxy-β-oxo-3-phenanthreneethane-sulfonic acid, sodium salt | white solid |
| 54 | 53 | dihydroxymethyl-3-phenanthryl ketone | mp 98–104° C. |
| 55 | 9-acetyl-anthracene | α-hydroxy-β-oxo-9-anthraceneethane-sulfonic acid, sodium salt | mp 180–200° C. |
| 56 | 2-acetyl-phenanthrene | α-hydroxy-β-oxo-2-phenanthreneethane-sulfonic acid, sodium salt | white solid |
| 57 | 56 | dihydroxymethyl 2-phenanthryl ketone | white solid |
| 58 | 2-acetyl-thiophene | 2-thiopheneglyoxylaldehyde | mp 90–91° C. |
| 59 | 3 | hydroxy [p-(phenylthio)benzoyl]-methanesulfonic acid, sodium salt | white solid |
| 60 | 25 | (p-benzylphenyl)gloxylaldehyde | mp 103–110° C. |
| 61 | 60 | p-benzlbenzyoxylhydroxy-methanesulfonic acid, sodium salt | mp 280–300° C. (dec.) |
| 62 | p-chlorophenoxy acetophenone | 4'-(p-chlorophenoxy)-2,2-dihydroxy-acetophenone | mp 109–122° C. |
| 63 | 62 | [p-(p-chlorophenoxy)benzoyl]hydroxy-methanesulfonic acid, sodium salt | mp <300° C. |
| 64 | p-tert-butylphenoxy acetophenone | [p-(p-tert-butylphenoxy)benzoyl]-hydroxy-methanesulfonic acid, sodium salt | mp 190–230° C. (dec.) |
| 65 | 64 | 4'-(p-tert-butylphenoxy)-2,2-dihydroxy-acetophenone | mp 82–87° C. |
| 66 | p-fluoro-acetophenone | (p-fluorophenyl)-glyoxal | mp 93–98° C. |
| 67 | 66 | p-fluorobenzoylhydroxy-methanesulfonic acid, sodium salt | mp 300° C. |
| 68 | 4-methoxy acetophenone | p-anisoylhydroxy-methanesulfonic acid, sodium salt | white solid |
| 69 | 68 | 2,2-dihydroxy-4'-methoxy-acetophenone | mp 79–81° C. |
| 70 | 12 | 4'-(hexadecyloxy)-2,2-dihydroxy-acetophenone | mp 91–94° C. |
| 71 | 70 | [p-(hexadecyloxy)benzoyl]hydroxy-methanesulfonic acid, sodium salt | white solid |
| 72 | p-fluoro-phenoxy acetophenone | [p-(p-fluorophenoxy)phenyl]glyxal | mp 102–104° C. |
| 73 | 72 | [p-(p-fluorophenoxy)benzoyl]hydroxy-methanesulfonic acid, sodium salt | mp <300° C. |
| 74 | 4 | 2,2-dihydroxy-4'-(p-methoxyphenoxy)-acetophenone | mp 115–119° |
| 75 | 74 | hydroxy[p-(p-methoxyphenoxy)benzoyl]-methanesulfonic acid, sodium salt | mp 180–190° (dec.) |
| 76 | n-butyloxy acetophenone | p-butoxyphenyl) glyoxal | mp 82–87° C. |
| 77 | 76 | p-butoxybenzoylhydroxy-methanesulfonic acid, sodium salt | white solid |

TABLE IV-continued

| Example | Intermediate Derivation | Product | Physical Constant |
|---|---|---|---|
| 78 | 5 | 4'-(p-bromophenoxy)-2,2-dihydroxy-acetophenone | mp 120–125° C. |
| 79 | 6 | [p-(p-tert-butylphenythio)benzoyl]-hydroxy methanesulfonic acid, sodium salt | 160° C. (dec.) |
| 80 | 7 | hydroxy[p-(p-methoxyphenythio)benzoyl]-methanesulfonic acid, sodium salt | mp 185–190° |
| 81 | 71 | [p-(decylamino)benzoyl]hydroxy-methane-sulfonic acid, sodium salt | white solid |
| 82 | 13 | 2,2-dihydroxy-4'-m-tolyloxy-acetophenone | mp 79–87° C. |
| 83 | 82 | hydroxy[p-(m-tolyloxy)benzoyl]-methane-sulfonic acid, sodium salt | mp 190–195° C. |
| 84 | 15 | 2,2-dihydroxy-4'-p-tolyloxy-acetophenone | mp 92–99° C. |
| 85 | 84 | hydroxy(p-tolyloxybenzoyl)-methane-sulfonic acid, sodium salt | mp 160–180° C. (dec.) |
| 86 | 8 | [p-(p-fluorophenylthio)benzoyl]hydroxy-methanesulfonic acid, sodium salt | mp 180–200° C. (dec.) |
| 87 | 9 | [p-(m-chlorophenoxy)benzoyl]hydroxy-methanesulfonic acid, sodium salt | mp 200–210° C. (dec.) |
| 88 | 87 | 4'-(m-chlorophenoxy)-2,2-dihydroxy-acetophenone | mp 138–150° C. |
| 89 | 14 | hydroxy [p-(p-tolylthio)benzoyl]-methanesulfonic acid, sodium salt | mp 180–200° C. (dec.) |
| 90 | m-methoxy-phenoxyacetophenone | hydroxy [p-(m-methoxyphenoxy)benzoyl]-methanesulfonic acid, sodium salt | mp 160–180° C. (dec.) |
| 91 | 1 | hydroxy (p-propoxybenzoyl)-methane-sulfonic acid, sodium salt | white solid |
| 92 | 91 | 2,2-dihydroxy-4'-propoxy-acetophenone | mp 79–81° C. |
| 93 | 10 | (p-butylaminobenzoyl)hydroxy-methane sulfonic acid, sodium salt | white solid |
| 94 | 11 | [p-(p-chlorophenylthio)benzoyl]hydroxy-methanesulfonic acid, sodium salt | mp 205–220° (dec.) |
| 95 | 18 | [p-(m-fluorophenoxy)benzoyl]hydroxy-methanesulfonic acid, sodium salt | mp <300° C. |
| 96 | 4'-pentyl-oxy-acetophenone | hydroxy (p-pentyloxybenzoyl)-methane-sulfonic acid, sodium salt | white solid |
| 97 | o-bromo-acetophenone | o-bromobenzoylhydroxy-methanesulfonic acid, sodium salt | white solid |
| 98 | 16 | hydroxy[p-(octyloxy)benzoyl]-methane-sulfonic acid, sodium salt | white solid |
| 99 | 98 | 2,2-dihydroxy-4'-(octyloxy)-acetophenone | mp 75–79° C. |
| 100 | p-hexadecyl-amino-acetophenone | 4'-hexadecylamino-2,2-dihydroxy-acetophenone | mp 87–89° C. |
| 101 | 5 | [p-(p-bromophenoxy)benzoyl]hydroxy-methanesulfonic acid, sodium salt | mp <300° C. |
| 102 | 3-(4-methyl-phenoxy)-acetophenone | α-hydroxy-3-(4-methylphenoxy)-β-oxo-benzeneethanesulfonic acid, sodium salt | white solid |
| 103 | m-(p-tert-butylphenoxy phenoxy) acetophenone | 3-[4-(1,1-dimethylethyl)phenoxy]-hydroxy- -oxo-benzeneethanesulfonic acid, sodium salt | white solid |
| 104 | p-decyl-amino-acetophenone | 4-(decylamino)-α-oxo-benzeneacetaldehyde | mp 88–90° C. |
| 105 | 100 | 4-(hexadecylamino)-α-hydroxy-β-oxo-benzeneethanesulfonic acid, sodium salt | mp 187–190° C. |
| 106 | p-chloro-acetophenone | p-chlorophenylglyoxal | mp 114–116° C. |
| 107 | 106 | (p-chlorobenzoyl)hydroxy-methanesulfonic acid, sodium salt | white solid |
| 108 | 35 | (4-biphenylcarbonyl)hydroxy-methane-sulfonic acid, sodium salt | mp <150° C. |
| 109 | 116 | 4'-chloro-α-hydroxy-β-oxo-4-biphenyl-ethanesulfonic acid, sodium salt | mp <200° C. |
| 110 | 113 | p-cyclohexylbenzoylhydroxy-methanesulfonic acid, sodium salt | mp 175–190° (dec.) |
| 111 | 117 | p-heptylbenzoylhydroxy-methanesulfonic acid, sodium salt | mp 165–180° C. |
| 112 | 119 | hydroxy(4'-methyl-4-biphenylcarbonyl)-methanesulfonic acid, sodium salt | mp 250° C. (dec.) |
| 113 | 4'bromo-2,3-dihydroxy-acetophenone | p-bromobenzoylhydroxy-methanesulfonic acid, sodium salt | mp 185–210° C. (dec.) |
| 114 | 26 | 4'-(o-bromophenyl)2,2-dihydroxy-acetophenone | white solid |
| 115 | 2-bromo-4'- | 2'-chloro-α-hydroxy-β-oxo-4-biphenyl- | mp 173° C. |

TABLE IV-continued

| Example | Intermediate Derivation | Product | Physical Constant |
|---|---|---|---|
| | (o-chloro-phenyl)-acetophenone | ethanesulfonic acid, sodium salt | (dec.) |

EXAMPLE 116

4'-(p-Chlorophenyl)-2,2-dihydroxy-acetophenone

A mixture of 9.28 g of 2-bromo-4'-(p-chlorophenyl)acetophenone (Example 22), 1.58 g of 89% phenol and 60 ml of dimethyl sulfoxide was stirred overnight then poured into ice water, giving a solid. The solid was triturated with methylene chloride and this solid was crystallized from acetone, giving the desired product as a beige solid, mp 275°–285° C.

Following essentially the procedure of Example 116 and using the indicated intermediates the products of Examples 117–119 given in Table V were obtained.

TABLE V

| Example | Intermediate Derivation | Product | Physical Constant |
|---|---|---|---|
| 117 | 24 | 4'-heptyl-2,2-dihydroxy-acetophenone | mp 73.5–76.5° C. |
| 118 | 23 | 4-cyclohexyl-2,2-dihydroxy-acetophenone | mp 87–105° C. |
| 119 | 19 | 2,2-dihydroxy-4'-p-tolyl-acetophenone | mp 105–140° C. |

EXAMPLE 120 p[[hydroxy(2-naphthoyl)methyl]amino]benzoic acid

A mixture of 7.28 g of 2,2-dihydroxy-2'-acetonaphthone (prepared from 2'-acetonaphthone by the procedure of Example 31), 4.11 g of p-aminobenzoic acid, 150 ml of tetrahydrofuran and 50 ml of water was refluxed under nitrogen for 4 hours, then cooled and filtered. The filtrate was evaporated to a solid which was recrystallized from acetone:water, giving the desired product, mp 138°–148° C. (dec.).

Following the essential procedure of Example 120 and using the indicated intermediates, the products of Example 121 and 122 given in Table VI were obtained.

TABLE VI

| Example | Intermediate Derivation | Product | Physical Constant |
|---|---|---|---|
| 121 | 35 | p-[α-hydroxy-p-phenyl-phenacyl)amino]benzoic acid | mp 166° C. |
| 122 | 30 | p-[[2-(2-dibenzofuranyl)-1-hydroxy-2-oxoethyl]amino]benzoic acid | mp 217–219° C. (dec.) |

EXAMPLE 123

Phenyl glyoxal hydrate

A 200 g portion of phenyl glyoxal was distilled in a chilled flask containing 800 ml of water. The suspension was then diluted with 2.5 liters of water, cooled and the desired product collected as a white solid, mp 74°–80° C.

EXAMPLE 124 p-[(α-Ethoxy-p-phenylphenacyl)amino]benzoic acid

A 16.0 g portion of p-[(α-hydroxy-p-phenylphenacyl)amino]benzoic acid (Example 121) was heated in an oil bath at 140°–150° C. and 14 mm for 5 hours to a constant weight. A 10.0 g portion of this solid was stirred with 100 ml of 95% ethanol for 16 hours. The solid was collected and dried, giving the desired product as a light brown solid, mp 179° C.

EXAMPLE 125

N-(α-Hydroxy-p-phenylphenacyl)sulfanilic acid, sodium salt

A mixture of 1.14 g of 4-biphenylglyoxal (Example 35), 0.77 g of sulfanilic acid, 3.9 ml of 1N sodium hydroxide, 10 ml of water, 10 ml of ethanol and 10 ml of dioxane was stirred overnight, filtered and the filtrate evaporated. The solid was reduced to a powder, stirred with 75 ml of acetone and the solid collected. This solid was stirred with 75 ml of methanol, filtered and the filtrate evaporated. The residue was slurried in methanol and the mixture filtered. The filtrate was diluted with 4 volumes of ether and the solid collected giving the desired product as a tan solid, mp 285°–310° C. (dec.).

EXAMPLE 126

Dihydroxymethyl-5-phenyl-2-thienyl ketone

A solution of 97 ml of 2-bromothiophene in 500 ml of ether was prepared. A 100 ml portion of this solution was added to 36.5 g of magnesium and the mixture was stirred until the reaction started. The remaining 400 ml of solution was added slowly and then the mixture was stirred 1.5 hours. A 113 ml portion of cyclohexanone was added dropwise, then the mixture was allowed to stand overnight. A mixture of 150 ml of concentrated hydrochloric acid in 300 ml of water was added and the mixture was allowed to stand for 67 hours. An additional 100 ml of concentrated hydrochloric acid was added and the layers were separated. The aqueous layer was extracted with three 100 ml portions of ether. These extracts were combined with the organic layer, filtered and distilled at 100°–120° C., 5 mm giving an oil.

A 111 g portion of this oil and 334 g of chloranil in 500 ml of toluene were heated on a steam bath for 4 hours and then filtered. The filtrate was extracted with three 250 ml portions of 1N sodium hydroxide. The organic phase was filtered and evaporated to an oil which was distilled at 114°–117° C. giving an oil.

To a mixture of 39.8 g of the above oil in 200 ml of acetic anhydride was added 12 drops of perchloric acid. The mixture was stirred 3 hours, then poured onto ice. The solid was collected, dissolved in methylene chloride, dried and filtered through hydrous magnesium silicate. Hexane was added to the filtrate which was then evaporated on a steam bath until crystals started to form. The mixture was cooled and the solid collected.

A mixture of 10.1 g of the above solid, 5.83 g of selenium dioxide, 3 ml of water and 50 ml of dioxane was reacted as described in Example 31, giving the desired product as a light tan crystalline solid, mp 124°–128° C.

EXAMPLE 127

α-Hydroxy-β-oxo-5-phenyl-2-thiopheneethanesulfonic acid, sodium salt

Dihydroxymethyl-5-phenyl-2-thienyl ketone was converted to the desired sodium salt by the procedure of Example 32 as a light tan crystalline solid, mp 300° C.

We claim:

1. The method of treating diabetes mellitus in a mammal in need of such treatment which comprises administering to said mammal an effective antidiabetic amount of α-hydroxy-β-oxo-3-biphenylethanesulfonic acid, sodium salt.

2. The method of treating hyperglycemia in a mammal in need of such treatment which comprises administering to said mammal an effective hypoglycemic amount of α-hydroxy-β-oxo-3-biphenylethanesulfonic acid, sodium salt.

* * * * *